(12) United States Patent
Fischer

(10) Patent No.: US 9,905,102 B2
(45) Date of Patent: Feb. 27, 2018

(54) OPEN SCATTERED LIGHT SMOKE DETECTOR AND TESTING DEVICE FOR AN OPEN SCATTERED LIGHT SMOKE DETECTOR OF THIS TYPE

(71) Applicant: Siemens Schweiz AG, Zurich (CH)

(72) Inventor: Martin Fischer, Buelach (CH)

(73) Assignee: SIEMENS SCHWEIZ AG, Zurich (CH)

( * ) Notice: Subject to any disclaimer, the term of this patent is extended or adjusted under 35 U.S.C. 154(b) by 141 days.

(21) Appl. No.: 15/148,072

(22) Filed: May 6, 2016

(65) Prior Publication Data

US 2016/0328936 A1    Nov. 10, 2016

(30) Foreign Application Priority Data

May 6, 2015    (EP) .................................... 15166565

(51) Int. Cl.
*G08B 17/10*    (2006.01)
*G08B 17/107*    (2006.01)
(Continued)

(52) U.S. Cl.
CPC .............. *G08B 17/107* (2013.01); *G01J 1/42* (2013.01); *G01N 21/53* (2013.01); *G08B 29/145* (2013.01);
(Continued)

(58) Field of Classification Search
None
See application file for complete search history.

(56) References Cited

U.S. PATENT DOCUMENTS 6,515,589 B2   2/2003   Schneider et al. ............ 340/630
8,587,442 B2  11/2013   Loepfe et al. ................ 340/628
(Continued)

FOREIGN PATENT DOCUMENTS

| EP | 1191496 A1 | 3/2002 | ............ G08B 17/107 |
| EP | 1583055 A2 | 10/2005 | ............ G08B 17/06 |
| EP | 2093734 A1 | 8/2009 | ............ G08B 17/107 |

OTHER PUBLICATIONS

European Office Action, Application No. 15166565.0, 5 pages, dated Nov. 16, 2015.

*Primary Examiner* — George Bugg
*Assistant Examiner* — Renee Dorsey
(74) *Attorney, Agent, or Firm* — Slayden Grubert Beard PLLC

(57) ABSTRACT

An open scattered light smoke detector for detecting smoke may include a light transmitter for emitting light, a light receiver spectrally matched to the light transmitter, and a control unit configured to repeatedly actuate the light transmitter, with a pulsed signal sequence, to emit corresponding light pulses, evaluate temporally a signal sequence received by the light receiver, and output a fire alarm if a received signal strength exceeds a minimum value for the smoke concentration. The control unit may be configured to switch the detector from a normal operating mode into a service mode if a phase angle between an emitted and received signal sequence, as determined on the detector side, increases by a minimum angular value which, in terms of the travel time, corresponds technically to an increase in the optical path length from the light transmitter to the light receiver of more than some predefined distance.

11 Claims, 2 Drawing Sheets

(51) Int. Cl.
*G08B 29/14* (2006.01)
*G01J 1/42* (2006.01)
*G01N 21/53* (2006.01)

(52) U.S. Cl.
CPC *G01J 2001/4242* (2013.01); *G01N 2201/125* (2013.01)

(56) References Cited

U.S. PATENT DOCUMENTS

| | | | |
|---|---|---|---|
| 2002/0186141 A1* | 12/2002 | Jen | G08B 17/10 340/630 |
| 2006/0114467 A1* | 6/2006 | Nicoli | G01N 21/51 356/450 |
| 2008/0018485 A1* | 1/2008 | Kadwell | G08B 17/107 340/630 |
| 2008/0150518 A1* | 6/2008 | Becker | G01N 15/1031 324/204 |
| 2012/0235822 A1* | 9/2012 | Barson | G08B 17/107 340/630 |

* cited by examiner

OPEN SCATTERED LIGHT SMOKE DETECTOR AND TESTING DEVICE FOR AN OPEN SCATTERED LIGHT SMOKE DETECTOR OF THIS TYPE

CROSS-REFERENCE TO RELATED APPLICATIONS

This application claims priority to EP Application No. 15166565.0 filed May 6, 2015, the contents of which are hereby incorporated by reference in their entirety.

TECHNICAL FIELD

The invention relates to an open scattered light smoke detector, which has a light transmitter for emitting light, in particular in the optically invisible region, and a light receiver which is spectrally matched to this. The detector incorporates a control unit which is linked to the light transmitter and the light receiver. This unit is equipped for actuating the light transmitter repeatedly, in particular periodically with a pulsed signal sequence, to emit corresponding light pulses and to evaluate a signal sequence received by the light receiver and to output a fire detector if a signal strength of the received signal sequence exceeds a minimum value for the smoke concentration.

Further, the invention relates to a testing device for testing an open scattered light smoke detector of this type.

The pulsed signal sequence is preferably a rectangular timing signal which actuates the light transmitter at the same timing cycle, e.g. via a switch, so that a sequence of periodic light pulses is generated in the light transmitter. After this, there follows a dark period. Technical signal filtering at the same clock frequency by the light receiver effectively suppresses light signals at other frequencies.

BACKGROUND

Open scattered light smoke detectors are described, for example, in the international patent application WO 2001/031602 A1 or in the European patent application EP 2 093 733 A1.

The European patent application EP 1 191 496 A1 likewise describes an open scattered light smoke detector. In this, an amplitude modulator in the an open scattered light smoke detector forms, from the electrical signal for the transmitter actuation, a sequence of pulses, and in doing so effects an amplitude modulation. In its simplest form, this is a switch, so that a sequence of periodic light pulses is generated in the light transmitter, and then a dark period is again effected, and this alternately in a cycle which is prescribed by the amplitude modulator. A processor then evaluates the received signals by comparison with these transmitted signals, which the amplitude modulator transmits directly to the processor. By this means, the processor is in a position, on the one hand, to make a determination of how far away an item is by reference to the phase shift between the emitted and received pulses and, on the other hand, to check whether the item is a smoke cloud or an object. In the case of a solid object, the width of the received pulse remains unchanged by comparison with the width of the emitted pulse (FIG. 6). On the other hand, if the emitted pulse sequence meets a smoke cloud, then the pulses in the emitted sequence of pulses scatter, and there is pulse dispersion, because there are many centers of scattering in the smoke cloud (FIG. 7). The width of the pulses received is then a measure of whether smoke is present or not.

SUMMARY

One embodiment provides an open scattered light smoke detector for the detection of smoke, with a detection space lying outside the detector, with an associated light transmitter for emitting light and with a light receiver which is spectrally matched to this, wherein the scattered light smoke detector has a control unit which is connected to the light transmitter and the light receiver, and wherein the control unit is equipped for actuating the light transmitter repeatedly with a pulsed signal sequence to emit appropriate light pulses and to evaluate temporally a signal sequence received by the light receiver, and to output a fire alarm if a signal strength of the received signal sequence exceeds a minimum value for the smoke concentration, wherein the control unit is configured to switch the scattered light smoke detector from a normal operating mode into a service mode if a phase angle, determined on the detector side, between an emitted and a received signal sequence increases by a minimum angular value which, in terms of travel time, corresponds technically to an increase in the optical path length from the light transmitter to the light receiver of more than 6 m, in particular of more than 10 m.

In one embodiment, the control unit is configured to switch the scattered light smoke detector into at least one further service mode, depending on the phase angle determined on the detector side, wherein there is assigned to the further service mode concerned a further minimum angular value, which is larger than the minimum angular value, and wherein the further minimum angular values concerned are different from each other.

In one embodiment, the control unit of the detector is configured to suppress individually for a particular service mode the output of a fire alarm in the event of a fire situation being detected.

In one embodiment, the detector has a phase determination system for the determination of a current phase angle between an emitted and a received signal sequence and wherein the phase determination system outputs a service signal if the current phase angle which is determined increases, in particular suddenly, by the minimum angular value or by at least one of the further minimum angular values.

In one embodiment, the minimum angular value lies in a range from 10° to 360°, e.g., at 180°±30°.

In one embodiment, the control unit is configured to switch the scattered light smoke detector, for a minimum time, from the normal operating mode into the relevant service mode and/or if the service mode concerned is already in effect to switch the scattered light smoke detector back into the normal operating mode again, if the phase angle determined on the detector side increases once again by the minimum angular value or by the relevant further minimum angular value.

In one embodiment, the control unit is configured to indicate visually and/or audibly at the detector that the service mode is in effect, and/or to signal that it is in effect via a connected wired or wireless reporting bus to a danger monitoring center.

In one embodiment, the control unit is configured, in the service mode, to actuate by means of a binary data signal the light transmitter or a further light transmitter of the detector, which encodes internal detector data, wherein the detector data includes the current signal strength of the received signal sequence, calibration data for the detector's optical path, configuration data, operating data, a positional specification for the detector mounting site, a serial number and/or a bus address of the detector.

In one embodiment, the data signal is encoded as a bit sequence, a Manchester code sequence, a biphase-mark code, a return-to-zero code, a pulse-position code or a pulse-width code.

In one embodiment, the data signal is based on a data transmission protocol for infrared communication, in particular on an IrDA standard or on a data transmission protocol for infrared remote controls.

Another embodiment provides a testing device for testing a scattered light smoke detector in accordance with one of the preceding claims, wherein the testing device has a light receiving unit and a light transmitting unit which are spectrally matched to the light transmitters and the light receiver of the scattered light smoke detector, wherein the testing device has a control system connected to these and wherein the control system is configured to output, by means of the light transmitting unit, a pulsed light signal which has been received by means of the light receiving unit, as a light signal delayed by at least the prescribed minimum angular value or by at least the relevant prescribed further minimum angular value.

In one embodiment, the testing device has an output unit on the user side and wherein the control system is configured to analyze the pulsed light signal which is received for a possible valid encoding, by which is or are encoded the current signal strength for the scattered light smoke detector as claimed in one of the claims 8 to 10 and/or the calibration data for the optical path of the scattered light arrangement, the configuration data, the operating data, the positional specification of the detector mounting site, the serial number and/or the bus address of the scattered light smoke detector.

In one embodiment, the control system is configured to adjust the transmitted signal level of the light transmitting unit and/or the phase shift for the time-delayed light signal which is to be emitted by means of the light transmitting unit, on the basis of a distance between the testing device and the scattered light smoke detector which is to be tested.

In one embodiment, the testing device has a distance measurement system for determining the distance between the testing device and the scattered light smoke detector which is to be tested and wherein the distance which is determined can be registered by the control system of the testing device.

In one embodiment, the testing device is a smartphone, a tablet PC or a notebook.

BRIEF DESCRIPTION OF THE DRAWINGS

Example aspects and embodiments of the invention are explained below with reference to the figures, in which.

DETAILED DESCRIPTION

Figure 1:
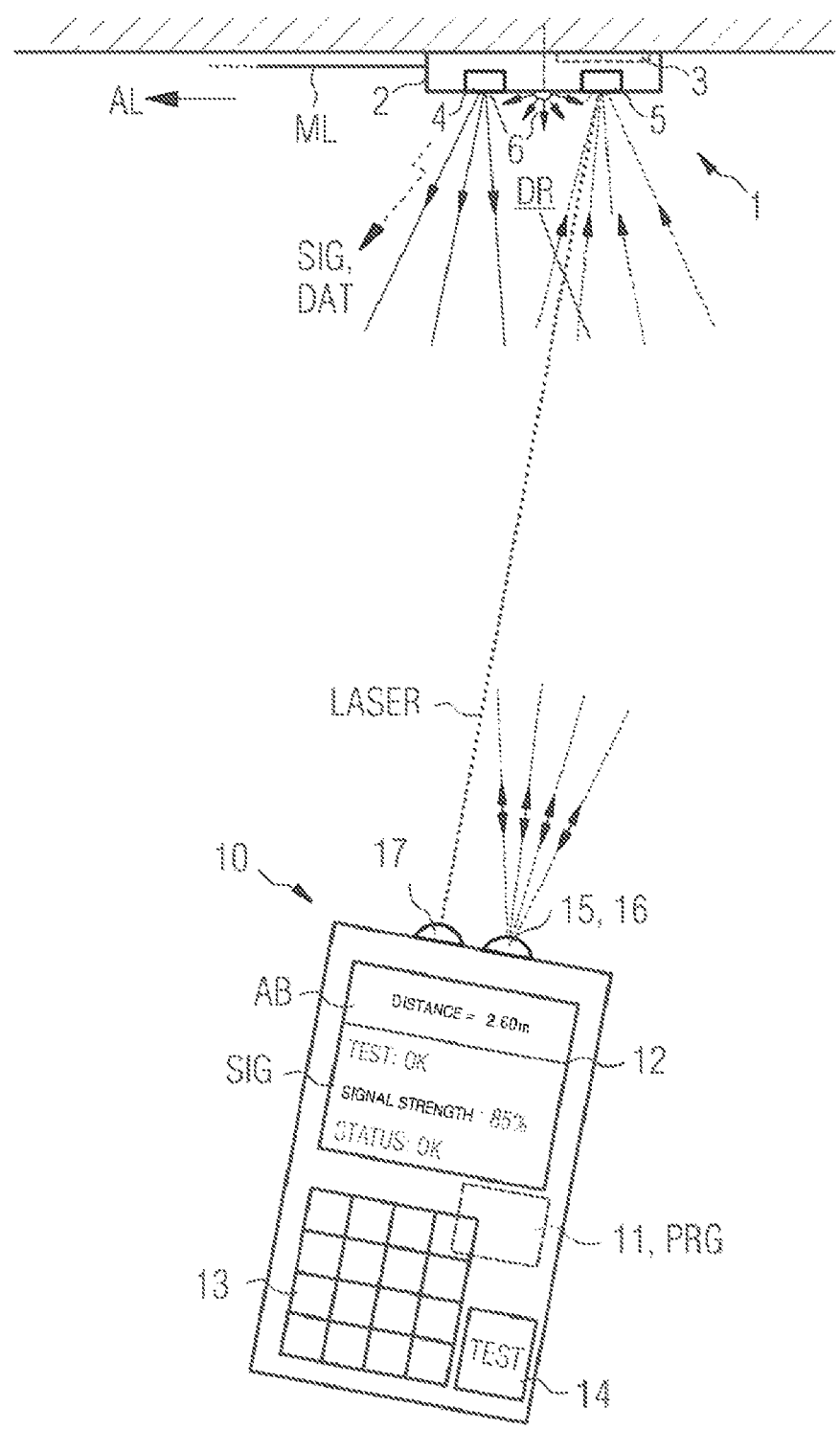
FIG. 1 shows an example open scattered light smoke detector and an associated testing device in accordance with one embodiment.

Embodiments of the invention provide an open smoke detector that can be tested in a simple manner.

Some embodiments provide a control unit configured to switch a detector from a normal operating mode into a (first) service mode if a phase angle determined on the detector side, between an emitted and a received signal sequence, changes by a (prescribed) minimum angular value which, in terms of travel time, corresponds to an increase in the optical path length from the light transmitter to the light receiver of more than 6 m, in particular of more than 10 m or 20 m, and preferably of more than 50 m.

What is meant by "normal operating mode" is that, in a case when fire is detected, the inventive detector outputs a fire alarm or fire report.

"Service mode" means any mode of the scattered light smoke detector which does not represent a normal operating mode. It can also be designated as a checking mode or test mode.

The term "optical path length" here means the path of the signal from the light emitter to the detection space, located in the open, as the scattered light center and back to the light receiver. Here, it can be assumed that there will always be a certain residual scattered light from the detection space which, even though very small in magnitude, is detectable by the light receiver.

Typically, the detection space for optical smoke detection lies about 5 to 10 cm in front of the detector. An increase in the optical path to 6 m or 10 m would thus imply that the scattered light center is located at a radial distance of 3 m or 5 m from the detector. The increase in the optical path length is also accompanied by an increase in the signal travel time, wherein the light of the signal sequence which is emitted and received back again propagates with the speed of light.

Embodiments of the invention are based on the recognition that an increase in the phase angle of this type, above all a sudden unusually large and hence implausible increase, can certainly not have been caused by an increase in the optical path length itself. A corresponding scattered light signal from a detection space at a distance of 3 m or 5 m, and in particular at a distance of 10 m or even 25 m, would be simply too limited for a reliable evaluation, and would be masked by ambient light in the optical spectrum of the light receiver. Consequently, this increase can be called on as a criterion for selectively exercising an effect on the operating mode of the inventive scattered light smoke detector, such as for example with the testing device provided in accordance with the invention for that purpose.

The unusual increase in the phase angle is of equal significance with an unusual increase in the signal travel time for a sequence of light pulses emitted by the light transmitter and scattered back to the light receiver from a remotely located object.

In this context, "sudden" means that such an increase in the phase angle is determined from one signal sequence interval to the following signal sequence interval, and is preferably constant over a few, e.g. in the range from 2 to 5, signal sequence intervals.

The control unit of the inventive detector can now be configured so that, for example, in the service mode a test of the alarm sounder is advantageously carried out, in that the detector outputs briefly an acoustic alarm, if appropriate with a greatly reduced volume. In this way, it is possible to forgo a test button.

Alternatively or additionally, the control unit can be configured to output briefly at the detector a visual alarm. It is possible to forgo a test button.

Alternatively or additionally, the control unit can be configured to speed up the output, in the service mode, of a fire alarm in that, for example, there is no further averaging over several measured values. This permits more rapid checking of the detector by a service technician who, for this purpose, can for example spray a test aerosol into the detection space.

Alternatively or additionally, the control unit can be configured to output, in the service mode, a test alarm or a test message to a higher level fire monitoring center.

Alternatively or additionally, the control unit can be configured to switch the detector into an inactive power-saving mode.

Typically, the control unit will periodically actuate the light transmitter with a pulsed signal sequence to emit corresponding light pulses, such as for example every 2 seconds. Here, a pulsed signal sequence can have several hundred up to a few thousand pulses. The duration of such a signal sequence itself lies in the range from 0.25 up to 2 milliseconds. The duration of an individual pulse lies typically in the range from 0.5 up to 2 microseconds. The ratio of the signal sequence period to the time duration of a signal sequence itself thus lies in the range from two up to three orders of magnitude higher.

The light transmitter previously mentioned is commonly a light emitting diode (LED), which preferably emits light in a range which cannot be seen visually by humans. The LED will preferably be an infrared LED or a UV LED. The light receiver will preferably be a photodiode or a photo-transistor. The control unit will preferably be processor-supported, and in particular a micro-controller.

In one embodiment, the control unit is configured to switch the scattered light smoke detector into at least one further service mode, depending on the phase angle determined on the detector side. Assigned to the further service mode concerned is a further minimum angular value, which is larger than the minimum angular value. The further minimum angular values concerned are different from each other.

By this means, the inventive scattered light smoke detector can, by means of a testing device provided for the purpose, be switched into various test modes, such as have been described above by way of example. The minimum angular value can then, for example, for a (first) service mode be at 30°. A further (second) minimum angular value can then be at 45° for a further (second) service mode, a further (third) minimum angular value for a further (third) service mode at 60° and a further (fourth) minimum angular value for a further (fourth) service mode at 75°.

Preferably, the control unit will be configured to switch the detector, in accordance with the phase angle which is determined, into the relevant service mode to which is assigned the highest minimum angular value. If the phase angle increases, as in the previous example, by 65°, then the control unit will switch the detector into the further (third) service mode, because the phase angle exceeds the further (third) minimum angular value of 60° which is assigned for this. However, the control unit will not switch the detector into the further (fourth) service mode, because the further (fourth) minimum angular value of 75° which is assigned for this is not reached.

In one embodiment, the control unit of the detector is configured to suppress individually in a particular service mode the output of a fire alarm in the event of a fire situation being detected. By this means a false alarm will advantageously not be triggered and output, e.g. during cleaning work on the detector using a duster. It is precisely such movements of a duster which have a similar pattern to those of fluctuating smoke clouds.

In one embodiment, the detector has a phase determination system for the determination of a current phase angle between an emitted and a received signal sequence. The phase determination system outputs a service signal, in particular, if the phase angle currently determined increases suddenly by the minimum angular value or by at least one of the further minimum angular values. The phase determination system can be integrated into the control unit itself, or can also be realized as software. The control unit is configured then to suppress internally, on the basis of the service signal, the output of the possible fire alarm.

Preferably, the minimum angular value will lie in a range from 10° to 360°, in particular at 180°±30°.

In one embodiment, the control unit is configured to switch the detector, for a minimum time, from the normal operating mode into the service mode and/or if the service mode is already in effect to switch the detector back into the normal operating mode again, if the phase angle determined on the detector side increases once again by the minimum angular value or by the relevant further minimum angular value.

By this means, the smoke detector can be selectively deactivated for a prescribed time, in order to suppress the triggering of an alarm if allowance must be made for a foreseeable, harmless or controlled incidence of smoke, such as for example during cooking or welding work. The prescribed time will preferably lie in a range from 5 up to 30 minutes.

The control unit is to be configured, in particular, to indicate optically and/or acoustically at the detector that the service mode is in effect and/or to signal this via a wired or wireless reporting bus to a fire monitoring center.

In one embodiment, the control unit is configured, in the service mode, to actuate by means of a binary data signal the light transmitter or a further light transmitter, such as for example an IR-LED, to monitor the surroundings for flow-screening objects. For this purpose, the data signal encodes internal detector data which includes the current signal strength of the received signal sequence, calibration data for the detector's optical path, configuration data, operating data, a positional specification for the detector mounting site, a serial number and/or bus address of the detector.

The current value of the signal strength is here determined on the basis of a received sequence of pulsed light signals, in particular of infrared light pulses which are emitted by a testing device, provided and configured for the testing of the inventive scattered light smoke detector.

Here, the data signal can be encoded as a bit sequence, as a Manchester code sequence, a biphase-mark code, a return-to-zero code, a pulse-position code or a pulse-width code. It can be based on a data transmission protocol for infrared communication, in particular on an IrDA standard. Alternatively, or additionally, it can be based on a data transmission protocol for infrared remote controls, in particular on an RC-5 or RC-6 data transmission protocol.

If the current signal strength for the received signal sequence is output in the service mode, such as for example in encoded form as a percentage value, then this value can be directly displayed on a testing device in accordance with the invention and can be taken into account by a specialist as part of the testing of the detector.

Furthermore, it is possible to output calibration data for the detector's optical path, such as for example detector-internal values for the amplification of the light receiver and for the driver stage of the light transmitter. This makes it possible, as explained later in detail, to perform a complete test of the detector's optical path with the help of the testing device.

It is also possible to output configuration data for the detector, such as for example the sampling frequency, the loudness of an acoustic alarm sounder, or an operating mode which has been set for the detector, such as for example robust operation in a rough environment or sensitive operation in an office.

It is furthermore possible to output operating data, such as for example fault data, event data or a current battery charge state, or a positional specification for the detector mounting site, for example in the form of GPS data, or a manufacturing serial number and/or a bus address of the detector for communication with a danger monitoring center.

Other embodiments provide a testing device for testing a scattered light smoke detector. The testing device may have a light receiving unit and a light transmitting unit which are spectrally matched to the light transmitter and the light receiver of the scattered light smoke detector. Furthermore, the testing device has a control system, such as for example a microcontroller, which is connected to the light receiving unit and to the light transmitting unit. This control system is configured to output as a delayed light signal, by means of the light transmitting unit, a pulsed light signal, in particular a pulsed infrared signal which has been received by means of the light receiving unit, delayed by at least the relevant prescribed minimum angular value or by at least the prescribed further minimum angular value.

By this means it is advantageously possible, as described in the introduction, to switch the open scattered light smoke detector which is to be tested from an operating mode into one or more service modes. It is also possible, for example, to suppress a fire alarm which may have been triggered during the testing of the scattered light smoke detector.

In one embodiment, the testing device has an output unit on the user side. The control system of the testing device is configured to analyze the pulsed, i.e. binary, light signal or infrared signal which is received for a possible valid coding, by which is encoded the current signal strength from the detector and/or the calibration data for the optical path of the scattered light arrangement, the configuration data, the operating data, the positional specification of the detector mounting site, the serial number and/or the bus address of the detector.

The display of the data cited above makes it advantageously possible for a service technician to make an on-site evaluation of the functional competence of the scattered light smoke detector. The service specialist can then immediately recognize whether, for example, the entire optical path of the scattered light smoke detector currently being tested still lies within permissible tolerances or not. The "optical path" includes all the optical and opto-electronic components of the scattered light arrangement, provided for the detection of smoke. Impermissible undershoots of the value of the received signal strength here point to parts of the optical path having become dirty, or an age-related degeneration of the opto-electronic components in the optical path of the scattered light arrangement of the detector.

In one embodiment, the control system is configured to adjust the transmitted signal level of the light transmitting unit and/or the time delay for the time-delayed light signal which is to be emitted by means of the light transmitting unit, on the basis of a distance between the testing device and the scattered light smoke detector which is to be tested. The distance can, for example, be input by a user through an input keyboard of the testing device.

It is well-known that the signal level of a light source drops off with the square of the distance from the light source. By an appropriate distance-dependent adjustment of the transmitted signal level of the light transmitting unit, the scattered light smoke detector which is to be tested will receive the light signal transmitted by the testing device at an essentially constant signal level. In the ideal case, the strength value of the signal currently received from the scattered light smoke detector, which is displayed on the display unit of the testing device, will be unchanged if there is an increase or decrease in the distance. The assumption here is that the light transmitting unit of the testing device is pointing, at least roughly, in the direction of the light receiver of the detector. Preferably, the detector's light receiver will have in front of it an optical arrangement, such as for example a concentrating lens, so that light with the same intensity from different directions can be detected at a roughly equal receiving level.

In embodiment, the testing device has a distance measurement system for determining the distance between the testing device and the scattered light smoke detector which is to be tested. The distance which is determined will be registered by the control system of the testing device. The distance measurement system can be, for example, a laser distance measurement device, such as a laser pointer.

In one embodiment, the testing device is a smartphone, a tablet PC or a notebook. In particular, these will then have an infrared interface, such as for example an IrDA interface.

FIG. 1 shows an example of an open scattered light smoke detector 1 and an associated testing device 10 in accordance with one embodiment. The scattered light smoke detector 1 shown in the upper part of FIG. 1 is affixed to a ceiling. The reference mark 2 indicates a detector housing. The detector 1 has in addition an electronic control unit 3 for the electrical actuation of an infrared LED 4 as the light transmitter with a pulsed signal sequence and for capturing, and performing a temporal evaluation on, a signal sequence received by an IR photodiode 5 as the light receiver. DR is the reference mark for a detection space, lying outside the detector housing 2, in which smoke is to be detected.

In the case when a fire alarm AL is detected, i.e. if an appropriate signal strength of the received signal sequence rises above a minimum value for the smoke concentration, this fire alarm AL is forwarded via a connected detector line ML or detector bus to a higher level fire alarm center. The reference mark 6 identifies a further light transmitter, in particular an infrared LED, which is provided, for example, for the monitoring of flow-masking objects, preferably within a radius of a half meter around the detector 1.

The control unit 3 may be configured to switch the scattered light smoke detector 1 from a normal operating mode into a service mode, if a phase angle between an emitted and a received signal sequence, determined on the detector-side, changes by a minimum angular value which corresponds in terms of the technical propagation time to an increase in the optical path length from the light transmitter to the light receiver of more than 6 m or 10 m. In this service mode there will be, in the present example, no output of a fire alarm AL. Instead of the fire alarm AL it is also possible, for example, for an item of test data to be output on the detector line ML, in order as necessary to inform the higher level fire alarm center.

This switch-over is effected by the inventive testing device 10 shown, which is provided and configured for the testing of a scattered light smoke detector 1 of this type. Such a testing device 10 incorporates a light receiving unit 16 and a light transmitting unit 15, which are spectrally matched to the light transmitters 4, 6 and to the light receiver 5 of the scattered light smoke detector 1. The two units 16, 15 can also be combined together in one component, e.g. as an IrDA interface. Preferably, all the opto-electronic components 4, 5, 6, 15, 16 mentioned here will be infrared components in the same wavelength range, such as for example at a typical wavelength of 940 nm. An electronic control system 11 of the testing device 10 is configured for outputting by means of the light transmitting unit 15 a pulsed light signal, received by the light receiving unit 16, as a light signal delayed by more than the prescribed minimum angular value.

The electronic control system 11 of the inventive testing device 10 can advantageously also be configured to modulate the amplitude of the light pulse sequence emitted, in order to imitate characteristic fluctuations of smoke clouds. Here, the fluctuations typically have a frequency in the region of a few Hertz, such as for example in the range from 0.5 to 2 Hz.

This pulsed, phase-delayed light signal output by the testing device 10 is now recognized as such by the inventive detector 1. The detector 1 thereupon switches over into the service mode. The control unit 3 is, in the present example, configured even in this service mode, to perform fire detection. For this purpose, the control unit 3 evaluates the signal strength SIG of the received signal sequence and, if applicable, any fluctuations in the signal sequence which are characteristic of smoke. The testing of the inventive scattered light smoke detector 1 is then terminated if, on the basis of the received signal sequence, a fire situation has been detected and this has been signaled optically and/or acoustically, for example at the detector 1. The output of this fire alarm AL to a higher level fire alarm center is here, in the service mode, suppressed. In this way, a functional test of the inventive scattered light smoke detector 1 is advantageously possible.

The reference mark PRG indicates further a program or an application which is loaded for the performance of the function of the control system 11 described above.

The testing device 10 shown has in addition a display unit 12, an input panel 13 on the user side in the form of a keyboard, together with a test button 14 which, in total, can also be realized by a touch-sensitive display unit, such as for example the touch screen on a smartphone. On the display unit 12 it is possible to output, as already illustrated, a measured distance value AB, a signal strength SIG determined by the scattered light smoke detector 1, together with further data from the detector 1. In the present example, the testing device 10 also even has a distance measurement device 17 for detecting the distance AB, between the testing device 10 and the detector 1 shown, by means of a laser beam LASER. For the arrangement shown in FIG. 1, the distance value of 2.60 meters determined metrologically is output on the display unit 12.

In some embodiments, the control unit 3 configured, in the service mode, to actuate the light transmitter 4 or the further light transmitter 6 with a binary data signal. This data signal encodes internal detector data DAT, i.e. the internal data of the detector 1 captured on the detector-side. These items of detector data DAT include, as shown, the current signal strength SIG of the received signal sequence of the detector 1. Over and above this, further detector data DAT can be output, such as for example calibration data for the optical path of the detector 1, configuration data, operating data, a positional specification for the detector mounting site, a serial number and/or a bus address of the detector.

Figure 2:
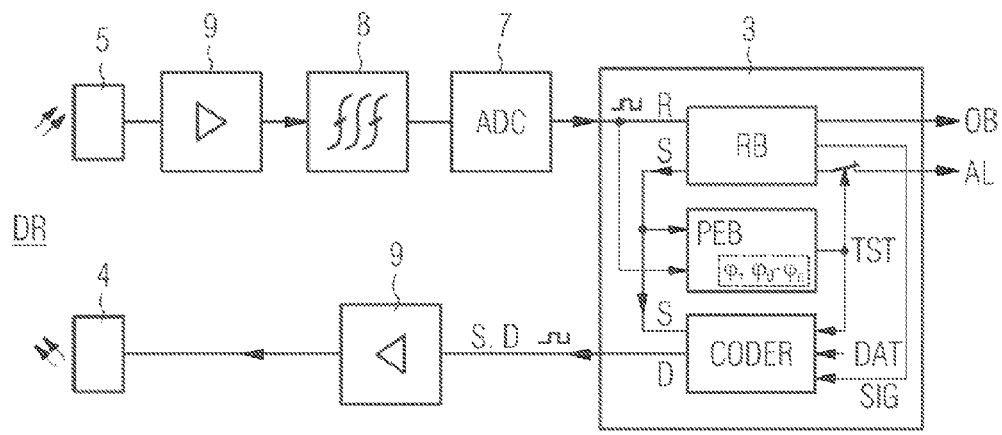
FIG. 2 shows a block circuit diagram of a scattered light smoke detector in accordance with one embodiment.

FIG. 2 shows a block circuit diagram of a scattered light smoke detector 1 in accordance with one embodiment. Shown in the left-hand part of the figure are the light transmitter 4 and the light receiver 5.

Figure 4:
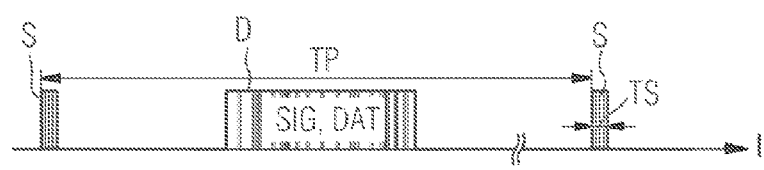
FIG. 4 shows an example of periodic pulsed signal sequences from a scattered light smoke detector with a binary data signal, inserted temporally between them, for the output of detector-side data in accordance with one embodiment.

In circuit before the light transmitter 4 is a signal processor, such as for example an amplifier 9, which outputs a periodic signal sequence S, which is output by the control unit 3, together with the binary data signal D. Here, the data signal D is a serial signal which encodes the detector data DAT and the signal strength SIG. For this purpose, the control unit 3 incorporates an encoding block CODER, realized as software, to which is fed on its input side the detector data DAT, the currently detected signal strength SIG as digital values, together with a switching or suppression signal TST for the presence of a service mode. If the service mode is present, or even independently of that, the encoding block CODER then converts the detector data DAT fed to it, together with the signal strength SIG, for example into a bit sequence, as a sequence for a Manchester code, a biphase-mark code, a return-to-zero code, a pulse-position code or a pulse-width code. As the associated FIG. 4 shows, the output of the binary data signal by the encoding block CODER is then preferably effected between two pulsed signal sequences S which are emitted.

The light receiver 5 which is shown is followed by a signal amplifier 9 for amplifying the light signal or infrared signal, as applicable, which had been received. The downstream bandpass filter 8 allows mainly only those signal portions to pass which agree with the clock frequency of the signal sequence S which is transmitted. In practice, initially only the alternating portion of the light receiver's received signal is considered by the signal technology, and is then filtered by means of a bandpass filter 8 matched to the clock frequency. A downstream A/D converter 7 converts the filtered signal into a sequence of digital values which, as the received signal sequence R, are correlated by signaling technology with the transmitted signal sequence S. The A/D converter 7 can also be an integral part of the control unit 3 itself. The signal which has been filtered and digitalized in this way is then computationally rectified and smoothed.

A smoke detection block RB of the control unit 3, realized for example as software, periodically generates a pulsed signal sequence S which is fed to the input side of the amplifier 9 for the light transmitter 4. The smoke detection block RB evaluates the associated signal sequence R which is received for quantities characteristic of a fire, and in the event that one is detected it outputs a fire alarm AL or an alarm message, as applicable. On its output side, the smoke detection block RB makes available a current signal strength value SIG, determined from the received signal sequence R, for further processing by the encoding block CODER. In parallel with this, the smoke detection block RB outputs a warning message OB in the event that flow-masking objects are detected in the region of the scattered light smoke detector 1, if a received signal sequence R remains essentially unchanged for a longer period of time. On the signal path for the alarm output there can be seen one more switch in accordance with the invention, which is not further labeled, which is provided in respect of its switching function of suppressing the fire alarm AL. In the present example, the corresponding switching signal TST is output by a further phase determination block PEB, realized as software. The switch will preferably again be realized as software, e.g. in the form of a variable.

The control unit 3 may be configured to suppress the output of the possible fire alarm AL if a phase angle φ determined by this phase determination system PEB increases by a minimum angular value $\phi_0$ or by at least the relevant prescribed further minimum angular value $\phi_1$-$\phi_n$. Here, "n" designates the number of possible further minimum angular values, and the corresponding number of possible further assigned service modes. This number will preferably be in a single-digit range. For the determination of the phase angle, the generally familiar lock-in filters are known which, because of the capabilities of today's micro-controllers as control units 3, can be realized by means of software. For this purpose, the phase determination block PEB evaluates the phase relationship between the transmitted pulsed signal sequence S and the received signal sequence R. If the increase which is determined in the phase angle φ exceeds the prescribed minimum angular value $\phi_0$, then on the output side the switching signal TST is output.

Figure 3:
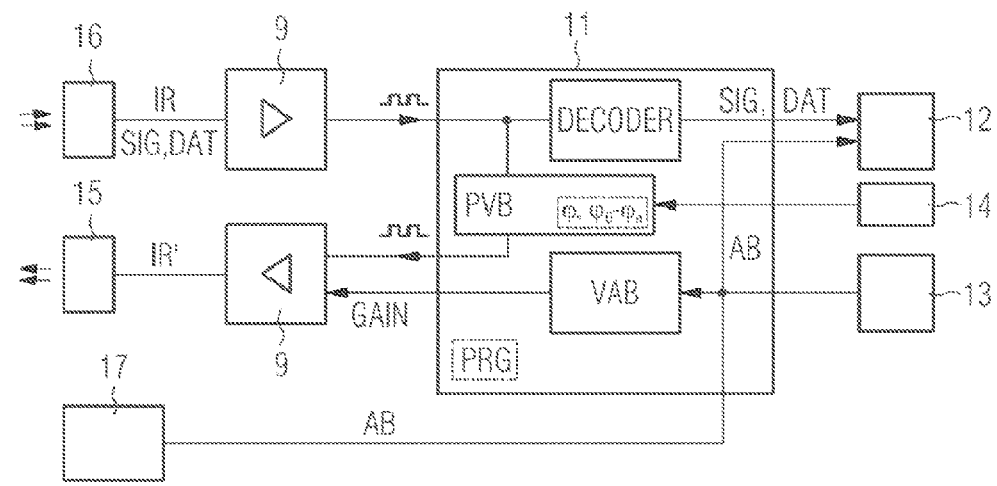
FIG. 3 shows a block circuit diagram of a testing device in accordance with the invention, for testing an open scattered light smoke detector in accordance with one embodiment.

FIG. 3 shows a block circuit diagram of a testing device 10 for testing an open scattered light smoke detector 1, according to one embodiment.

In the left-hand part of FIG. 3, the reference mark 15 identifies a light transmitting unit 15 and 16 a light receiving unit.

The light receiving unit 16 is spectrally tuned to the light transmitter of the scattered light smoke detector which is to be tested and for the reception of a pulsed infrared signal IR, which is output periodically by the inventive scattered light smoke detector and which can be encoded with the current signal strength SIG together with detector data DAT. The infrared signal IR which is received is first amplified and processed, such as for example by means of a comparator. The signal thus digitalized is fed to a decoding block DECODER in the control system 11, realized as software. The decoding block DECODER is configured to analyze the pulsed infrared signal IR which has been received for a possible valid coding, by which are encoded the current signal strength SIG of the scattered light smoke detector 1 and/or the calibration data of the optical path for the scattered light arrangement, the configuration data, the operating data, the positional specification of the detector mounting site, the serial number and/or the bus address of the scattered light smoke detector. In the event of a valid decoding, the decoded signal strength value SIG or the detector data DAT, as applicable, is output on the display unit 12 of the testing device 10.

In parallel with this, the digitalized signal is fed to a delay block VB, realized as software in the control system 11. In the event that the test button 14 on the testing device 10 had been pressed to start the test, this outputs to a downstream amplifier 9 the pulsed infrared signal IR which had been received, delayed by the prescribed minimum angular value $\phi_0$. The amplifier 9 amplifies the delayed infrared signal IR' as a function of a level of amplification GAIN, and then outputs this to the light transmitting unit 15.

Via the input panel 13 on the user side, which is in the form of a keyboard, the number for a further service mode can also be output. It the test button 14 on the testing device 10, for starting the test, is then pressed, the pulsed infrared signal IR which has been received is then output to the downstream amplifier 9, delayed by the prescribed further minimum angular value $\phi_1$-$\phi_n$ which corresponds to the number input.

VAB identifies an amplification adjustment block, which determines the level of amplification GAIN as a function of a detected or measured value of the distance AB from the testing device 10 to the detector 1 and outputs it to the amplifier 9, in order thereby to adjust appropriately the signal level of the light pulses which are emitted. The level of amplification GAIN can also be altered for the purpose of amplitude modulation, for the imitation of fluctuations which are characteristic of smoke damage. The distance value AB can, as previously described, be determined metrologically by means of a distance measurement system 17, or can be input on the user side through a keypad 13 on the testing device 10.

FIG. 4 shows an example of a periodically pulsed signal sequence S from a scattered light smoke detector 1 with a binary data signal D temporally interposed in it for the output of the detector-side data DAT.

TP indicates the period of the pulsed signal sequence S. This typically lies in a range from 1 to 10 seconds. TS labels the duration of the transmission time for an individual signal sequence. This typically lies in a range from 0.5 to 2 milliseconds.

In one embodiment, between two pulsed signal sequences S which are emitted, a pulsed data signal D is output, which encodes the current signal strength SIG together with the detector data DAT. The duration of such a data signal D depends on the quantity of data, i.e. on the number of data items transmitted together with their digital resolution. The transmission of the data will preferably be effected in modulated form with a carrier frequency of, for example, 36 or 40 kHz. If, for example, a time span of 1 millisecond is chosen for the carrier-frequency modulated transmission of a single bit, then there is, for example, no problem in transmitting 1000 bits between two signal sequences S with a period TP of 2 seconds.

The transmission of the detector data DAT can in each case be effected between two signal sequences S. In order to minimize the load on the scattered light smoke detector 1, it can be effected only at every second, third, fourth period, etc. up to the 50th period between two signal sequences S.

The transmission of the detector data DAT can be based on a data transmission protocol for infrared communications, in particular on an IrDA standard or on a data transmission protocol for infrared remote controls. The data transmission can be effected preferably only when the inventive scattered light smoke detector 1 has been switched into a service mode by means of the testing device 10.

The data can, independently of this, also be transmitted in the normal operating mode, and this for example in every period or only in each second, third, fourth period, etc., up to the 50th period between two signal sequences S, in order to keep the load on the scattered light smoke detector 1 as low as possible.

LIST OF REFERENCE MARKS

1 Open scattered light smoke detector
2 Detector housing
3, 11 Control unit, control system, micro-controller
4 Light transmitter, LED, IRED
5 Light receiver, photodiode, IR photodiode
6 Environmental light transmitter, IRED
7 A/D converter
8 Bandpass filter
9 Signal processor, comparator, amplifier
10 Testing device, smartphone
12 Display unit, display 13 Keypad, input panel
14 Keys, test start key
15 Light transmitting unit, LED, IRED
16 Light receiving unit, photodiode, IR photodiode
17 Distance measurement system, gap meter
AB Distance value
AL Fire alarm, alarm message, warning message
CODER Encoding block
D Binary data signal
DAT Detector data
DECODER Decoding block
DR Detection space, scattered light region
GAIN Level of amplification
IR Infrared signal, light signal
IR' Phase delayed infrared signal, light signal
LASER Laser beam
ML Detector line, detector bus, two-wire line
OB Warning message
PEB Phase determination block
PRG Program, application
R Received signal sequence
RB Smoke detection block
S Pulsed signal sequence, transmitted signal sequence
SIG Signal strength value, signal strength
t Time, time axis
TEST Test button, depressed
TP Period, duration of period
TS Duration of transmission
TST Switchover signal, service signal
VAB Amplification adjustment block
VB Delay block
$\phi$ Phase angle
$\phi_0$ Minimum angular value
$\phi_1, \phi_2, \phi_n$ Further minimum angular values

What is claimed is:

1. An open scattered light smoke detector for detecting smoke, comprising:
a light transmitter configured to emit light,
a light receiver that is spectrally matched to the light transmitter,
a control unit connected to the light transmitter and the light receiver, and configured to:
actuate the light transmitter repeatedly with a pulsed signal sequence to emit appropriate light pulses,
evaluate temporally a signal sequence received by the light receiver, and
output a fire alarm in response to determining that a signal strength of a received signal sequence exceeds a minimum value for smoke concentration, and
switch the scattered light smoke detector from a normal operating mode into a service mode in response to detecting that a phase angle, determined on the detector side, between an emitted signal sequence and a received signal sequence increases by a minimum angular value which, in terms of travel time, corresponds with an increase in an optical path length from the light transmitter to the light receiver of more than 6 m.

2. The detector of claim 1, wherein the control unit is configured to switch the scattered light smoke detector into at least one further service mode, depending on the phase angle determined on the detector side,
wherein a further minimum angular value is assigned to the further service mode, which further minimum angular value is larger than the minimum angular value.

3. The detector of claim 1, wherein the control unit is configured to suppress, for a particular service mode, the output of a fire alarm in the event of a fire situation being detected.

4. The detector of claim 1 including a phase determination system configured to determine a current phase angle between an emitted and a received signal sequence, and
wherein the phase determination system outputs a service signal in response to an increase in the determined current phase angle by at least the minimum angular value.

5. The detector of claim 4, wherein the minimum angular value lies in a range from 10° to 360°.

6. The detector of claim 1, wherein the control unit is configured to switch the scattered light smoke detector, for a minimum time, between a normal operating mode a relevant service mode in response to the phase angle determined on the detector side increasing again by the minimum angular value.

7. The detector of claim 1, wherein the control unit is configured to generate a visual or audible indication that the service mode is in effect.

8. The detector of claim 1, wherein the control unit is configured, in the service mode, to actuate the light transmitter or a further light transmitter of the detector using a binary data signal, wherein the binary data signal encodes internal detector data that includes at least one of a current signal strength of the received signal sequence, calibration data for an optical path of the detector, configuration data, operating data, a positional specification for a detector mounting site, a serial number, or a bus address of the detector.

9. The detector of claim 8, wherein the data signal is encoded as a bit sequence, a Manchester code sequence, a biphase-mark code, a return-to-zero code, a pulse-position code, or a pulse-width code.

10. The detector of claim 8, wherein the data signal is based on an IrDA standard for infrared communication or on a data transmission protocol for infrared remote controls.

11. The detector of claim 4, wherein the minimum angular value lies in a range of 180°±30°.

* * * * *